(12) United States Patent
Harle (10) Patent No.: US 9,352,394 B2
(45) Date of Patent: May 31, 2016

(54) NANO AGGREGATES OF MOLECULAR ULTRA SMALL CLUSTERS OF NOBLE METALS AND A PROCESS FOR THE PREPARATION THEREOF

(71) Applicant: Council of Scientific and Industrial Research, New Delhi (IN)

(72) Inventor: Arti Harle, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 14/415,312

(22) PCT Filed: Feb. 19, 2014

(86) PCT No.: PCT/IN2014/000102
§ 371 (c)(1),
(2) Date: Jan. 16, 2015

(87) PCT Pub. No.: WO2014/128722
PCT Pub. Date: Aug. 28, 2014

(65) Prior Publication Data
US 2015/0174657 A1    Jun. 25, 2015

(30) Foreign Application Priority Data
Feb. 19, 2013    (IN) .............................. 468/DEL/2013

(51) Int. Cl.
*B22F 9/24* (2006.01)
*B22F 1/00* (2006.01)
*B82Y 40/00* (2011.01)
*B82Y 5/00* (2011.01)

(52) U.S. Cl.
CPC ............. *B22F 1/0018* (2013.01); *B22F 1/0096* (2013.01); *B22F 9/24* (2013.01); *B82Y 5/00* (2013.01); *B82Y 40/00* (2013.01); *Y10S 977/774* (2013.01); *Y10S 977/896* (2013.01); *Y10T 428/2982* (2015.01)

(58) Field of Classification Search
None
See application file for complete search history.

(56) References Cited

U.S. PATENT DOCUMENTS

2013/0023714 A1* 1/2013 Johnston .............. A61K 9/0009
600/1

FOREIGN PATENT DOCUMENTS

| WO | WO-2012/028936 | 3/2012 |
|----|----|----|
| WO | WO-2014/128722 | 8/2014 |

OTHER PUBLICATIONS

"International Application No. PCT/IN2014/000102, International Search Report and Written Opinion mailed Aug. 6, 2014", (Aug. 6, 2014), 11 pgs.

(Continued)

*Primary Examiner* — Alexandre Ferre
(74) *Attorney, Agent, or Firm* — Schwegman, Lundberg & Woessner, P.A.

(57) ABSTRACT

The present invention discloses size controlled and stabilized nano-aggregates of molecular ultra small clusters of noble metals and a process for the preparation thereof. The present invention discloses single source multicolor noble metal spherical and uniform nano aggregates of 10-22 nm made up of discrete molecular ultra small noble metal (Nb) nanoclusters (MUSNbNC's) of 1-6 atoms. The MUSNbNC's are capped with amine/DCA (dicarboxy acetone) group acting as a steric and kinetic hindrance for core growth suppressing the further autocatalysis and conversion of super critical nucleus or growth by ripening and formation of nanoparticles and thus having intense fluorescence.

10 Claims, 9 Drawing Sheets

(56) References Cited

OTHER PUBLICATIONS

Alkilany, Alaaldin M., et al., "Toxicity and cellular uptake of gold nanoparticles: what we have learned so far?", J Nanopart Res (2010) 12:2313-2333, (Apr. 6, 2010), 2313-2333.
Borodko, Yuri, et al., "From Single Pt Atoms to Pt Nanocrystals: Photoreduction of Pt 2+ Inside of a Pamam Dendrimer", The Journal of Physical Chemistry Letters, vol. 3, No. 2, (Jan. 19, 2012), 236-241.
Chithrani, B. Devika, et al., "Elucidating the Mechanism of Cellular Uptake and Removal of Protein-Coated Gold Nanoparticles of Different Sizes and Shapes", Nano Letters, vol. 7, No. 6, 1542-1550 (2007), (Mar. 26, 2007), 1542-1550.
Daniel, Marie-Christine, et al., "Gold Nanoparticles: Assembly, Supramolecular Chemistry, Quantum-Size-Related Properties, and Applications toward Biology, Catalysis, and Nanotechnology", Chem. Rev. 2004, 104, 293-346, (2004), 293-346.
Deshpande, Aniruddha S., et al., "Sulfur Nanoparticles Synthesis and Characterization from H2S Gas, Using Novel Biodegradable Iron Chelates in W/O Microemulsion", Nanoscale Res Lett (2008) 3:221-229, (2008), 221-229.
Diez, Isabel, et al., "Fluorescent Silver Nanoclusters", Nanoscale, vol. 3, No. 5, (Jan. 1, 2011), 1963-1970.
Diffey, B. L., et al., "Ultraviolet radiation physics and the skin", Phys Med Biol. May 1980;25(3):405-26, (May 1980), 405-26.
Gonzalez, Beatriz Santiago, et al., "One Step Synthesis of the Smallest Photoluminescent and Paramagnetic PVP-Protected Gold Atomic Clusters", ACS Nano Lett. 2010, 10, 4217-4221, (Sep. 13, 2010), 4217-4221.
Huang, Chih-Ching, et al., "Bioconjugated Gold Nanodots and Nanoparticles for Protein Assays Based on Photoluminescence Quenching", Anal. Chem. 2008, 80, 1497-1504, (Mar. 1, 2008), 1497-1504.
Jain, Prashant K., et al., "Noble Metals on the Nanoscale: Optical and Photothermal Properties and Some Applications in Imaging, Sensing, Biology, and Medicine", Accounts of Chemical Research, 1578-1586, Dec. 2008, vol. 41, No. 12, (Dec. 2008), 1578-1586.
Laaksonen, Timo, et al., "Stability and Electrostatics of Mercaptoundecanoic Acid-Capped Gold Nanoparticles with Varying Counterion Size", Chem PhysChem 2006, 7, 2143-2149, (2006), 2143-2149.
Lin, C. A.J., et al., "Fluorescent Gold Nanoclusters Synthesis and Bioconjugation for Cellular Labeling", ESBME-Peter, (2010), 4 pgs.
Lin, Cheng-An J., et al., "Synthesis of Fluorescent Metallic Nanoclusters toward Biomedical Application: Recent Progress and Present Challenges", Journal of Medical and Biological Engineering, 29(6): 276-283, (Nov. 20, 2009), 276-283.
Lin, Jun, et al., "Formation of ordered arrays of gold nanoparticles from CTAB reverse micelles", Materials Letters 49 Ž2001. 282-286, (Jul. 2001), 282-286.
Muhammed, Madathumpady Abubaker Habeeb, et al., "Bright, NIR-Emitting Au23 from Au25: Characterization and Applications Including Biolabeling", Chem. Eur. J. 2009, 15, 10110-10120, (2009), 10110-10120.
Pan, Yu, et al., "Size-Dependent Cytotoxicity of Gold Nanoparticles", small 2007, 3, No. 11, 1941-1949, (2007), 1941-1949.
Petroski, Janet, et al., "The coordination chemistry of gold surfaces: Formation and far-infrared spectra of alkanethiolate-capped gold nanoparticles", Journal of Organometallic Chemistry, 2009, 694, 1138-1143, (2009), 1138-1143.
Ramsay, D. L., et al., "Abstract: Ultraviolet-B phototherapy for early-stage cutaneous T-cell lymphoma", Arch Dermatol. Jul. 1992;128(7):931-3 [abstract], (Jul. 1992), 931-3.
Schaeublin, Nicole M., et al., "Does Shape Matter? Bioeffects of Gold Nanomaterials in a Human Skin Cell Model", Langmuir 2012, 28, 3248-3258, (2012), 3248-3258.
Shang, Li, et al., "Ultra-small Fluorescent Metal Nanoclusters: Synthesis and Biological Applications", Nano Today, vol. 6, No. 4, (Jun. 19, 2011), 401-418.
Shi, Weili, et al., "Gold nanoparticles surface-terminated with bifunctional ligands", Colloids and Surfaces A: Physicochem. Eng. Aspects 246 (2004) 109-113, (2004), 109-113.
Tojo, Concha, et al., "Surfactant Effects on Microemulsion-Based Nanoparticle Synthesis", Materials 2011, 4, 55-72; doi:10.3390/ma4010055, (Dec. 29, 2010), 55-72.
Tsukuda, Tatsuya, "Toward an Atomic-Level Understanding of Size-Specific Properties of Protected and Stabilized Gold Clusters", Bull. Chem. Soc. Jpn., 2012, 85 (2), pp. 151-168, (Feb. 10, 2012), 151-168.
Winnik, Francoise M., et al., "Quantum Dot Cytotoxicity and Ways To Reduce It", Accounts of Chemical Research, 672-680, 2013, vol. 46, No. 3, (Jul. 9, 2012), 672-680.
Zhang, Xiao-Dong, et al., "Size-dependent radiosensitization of PEG-coated gold nanoparticles for cancer radiation therapy", Biomaterials, 33, 6408-6419 (2012), (2012), 6408-6419.
Zheng, Jie, et al., "Different sized luminescent gold nanoparticles", Nanoscale, 2012, 4, 4073-4083, (Jun. 2012), 4073-4083.
Zielinska-Jurek, Anna, et al., "Preparation and Characterization of Monometallic (Au) and Bimetallic (Ag/Au) Modified-Titania Photocatalysts Activated by Visible Light", Applied Catalysis B: Environmental, vol. 101, No. 3-4, (Jan. 14, 2011), 504-514.

\* cited by examiner

NANO AGGREGATES OF MOLECULAR ULTRA SMALL CLUSTERS OF NOBLE METALS AND A PROCESS FOR THE PREPARATION THEREOF

PRIORITY CLAIM TO RELATED APPLICATIONS

This application is a U.S. national stage application filed under 35 U.S.C. §371 from International Application Serial No. PCT/IN2014/000102, which was filed Feb. 19, 2014, and published as WO 2014/128722 on Aug. 28, 2014, and which claims priority to India Application No. 468/DEL/2013, filed Feb. 19, 2013, which applications and publication are incorporated by reference as if reproduced herein and made a part hereof in their entirety, and the benefit of priority of each of which is claimed herein.

FIELD OF INVENTION

The present invention relates to the size controlled and stabilized nano-aggregates of molecular ultra small clusters of noble metals and a process for the preparation thereof. Particularly the present invention relates to the single source multicolor noble metal spherical and uniform nano aggregates of 10-22 nm made up of discrete molecular ultra small noble metal (Nb) nanoclusters (MUSNbNC's) of 1-6 atoms. The MUSNbNC's are capped with amine/DCA (dicarboxy acetone) group acting as a steric and kinetic hindrance for core growth suppressing the further autocatalysis and conversion of super critical nucleus or growth by ripening and formation of nanoparticles and thus having intense fluorescence. The invention more specifically relates to gold/silver/platinum 10-22 nm spherical nano aggregates capped and stabilize at fringes with amine or DCA along with the oxyethylene group. The molecular ultra small clusters in a discrete form and controlled size of these Nano aggregates thus shows the quantum confinement effect. Hence, these noble metal nano clusters are having potential applications in biomedical like UV & photo therapy, in case of cutaneous lymphoma, biosensing, biolabeling/bioimaging applications. The 10-22 nm nano aggregates of discrete MUSAuNC's after capping with mercaptoundeconic acid (MUDA) shows increase in fluorescent emission by 6 times and which are stable at 3-4 acidic pH and at room temperature (~25°)

BACKGROUND OF THE INVENTION

Bio-sensing requires surface functionalization to detect a particular target molecule or ion. The surface has to be uniform, consistent and should have an ability to get modified without altering the original properties with respect to a target ion or molecule to be detected. Uniformity is of utmost importance for unconstrained and clutter-free binding of the target bio-molecule; small size, non toxicity to use as a fluorescent probe. These properties are important in achieving sensitivities of the order of $10^{-8}$-$10^{-9}$ M, especially in the case of piezo-electric sensors and also as a florescent chip as many metal ions plays vital role at extremely low concentrations during patho-physiology. The principal aim was dynamic utilization of noble metal particles with single domain synthesis and sample preparation.

Gold Nano Particles (AuNPs) are potential candidates for the development of nano-bio-sensors, diagnostic and therapy as they have been widely used in understanding the biological processes and also in diversified biomedical applications. AuNP's have attractive features such as, inert, easy and versatile surface chemistry to modify, biocompatibility negligible toxicity and researchers have gained enough experiences in synthesizing different size and shapes of AuNP's in controllable manner. Further, AuNP's are having very high sensitivity towards biomolecule, tuned SPR/luminescent, retention of bioactivity and opportunity for 3D imaging are important characters as a fluorescent probe/marker. Reliable and high-yielding methods for the synthesis of AuNP's, including those with spherical and non spherical shapes, have been developed over the last century. It is necessary to synthesize the nanomaterial for bioconjucation which can be universally used as a tracer as well in therapy. The very small nanoparticles, clusters and nanoroads shows visible to IR fluorescence. However small nanoparticles, clusters and nanorod's shows some form of toxicity. As the size increases due to the autocatalysis they convert to form the stable super critical nucleus showing surface plasmon; 5-25 nm particles shows the surface plasmon at 510-540 nm (Concha Tojo et al; Materials; 2011, 4, 55-72) and diminishing the fluorescent property, as the fluorescence is the function of molecule like electronic structures and quantum confinement effect which is observed in very small nanoparticles. (Tatsuya Tsukuda, Bull. Chem. Soc. Jpn., 2012, 85 (2), 151-168).

Ref made to Beatriz Santiago Gonzalez et al: ACS Nano lett. 2010, 10, 4217-4221 where Nonoclusters of gold particles capped with PVP is reported. Due to the weak bonding of PVP mass spectra only shows the peak related to $Au_2$ and $Au_3$ and the theoretical calculation using the Jellium model shows fluorescence emission at 293 nm and 336 nm which are related to clusters of $Au_2$ and $Au_3$. It showed UV (300 to 400 nm) emission from $Au_2$ to $Au_{11}$ PVP clusters however such small clusters are difficult to characterize and handle to utilize in any kind of applications. In the present invention the surface capped nano aggregates of ultra small clusters which are also stabilized by amine or DCA of reducing agent and hindering the further growth having luminescent properties of quantum clusters with size of 10-22 nm and shows UV emission at 300-335 nm, no plasma resonance and $2^{nd}$ order visible emission at 590-650 nm resemble to the nanoparticles or super critical nucleus are mentioned.

However recently, numerous studies have shown that size and capping agent of nanoparticles play an important role in cellular uptake and cytotoxicity; (B. Devika Chithrani and W. C. W. Chan; ACS Nanolett. 2007, 7(6), 1542-1550; Yu Pan; Willi Jahnen Dechent; Small, 2007, 3(11), 1941-1949 and Catherine J. Murphy; J Nanopart Res; 2010, 12, 2313-2333); X. D. Zhang et al; biomaterials; 2012, 33, 6408-6419) they have also shown that 10-27 nm size range of AuNP are most biocompatible and having negligible toxicity. Another problem with the small gold nano crystals is toxicity and difficulty in handling the very small size nano clusters. It was reported that 1.4 nm diameter particles were toxic, whereas 15 nm diameter particles were nontoxic, even at up to 100-fold higher concentrations. Particles above 5 nm are non fluorescent. Nanorod's are having the SPR and also the luminescence near IR and potential candidates for photothermal therapy against cancer but shows the toxicity by formation of reactive oxygen species (Nicole M. Schaeubin et al ACS, langmuire 2012, 28, 3248-3258). QD's are excellent probe due to distinctive quantum confinement effect and tunable and high photo luminescence however its toxic effects are of serious concern especially for bioapplications. (Francoise M. Winnik et al; ACS accounts of chemical research; 2013, 46 (3), 672-680).

Walter H. Chang et al; J. Medcal and biological Engg.; 2009, 29(6), 276-283 shows the blue, green and red emission by using the various capping agent and etching the NP's and final size of these nanocluster lies in the range of 1-3.5 nm however being very small they may lend the toxic effect.

Huan-Tsung Chang et al; Anal Chem.; 2008, 80, 1497-1504 synthesized 2.9 nm brightly luminescent MUDA capped Au nanodots which are stable for three months when stored in dark and at 4° C. Review by Didier Astruc et al; Chemi rev.; 2004, 104; 293-346 showed the aggregation of MUDA capped AuNP in acidic condition. C. A. J. Lin et al ESBME-Peter; AuNP capped with MUDA using tetraborate buffer, 9.2 pH. AuNP's 3.1 nm capped with MUDA shows the agglomeration when synthesized at room temperature as compared the cold synthesis (Mark T. Swihart, Colloids and Surfaces A: Physicochem Eng. Aspects 2004. 246; 109-113).

Alexander Gaiduk et al; publication no. WO 2012028936 A1 and application number: PCT/IB2011/002003 showed the green and red emission by using the organic solvent and photo thermal microscopy showed the enhancement in fluorescence in solid state. They coated the glass surface with glycerol. Fluorescence was not observed when water was used. However we do not have any such kind of restrictions, instrumentation and no photo-thermal therapy was needed. The particles are fluorescent in both solid and liquid state.

These problems are of a great challenge if the AuNP's are to be used in biological systems especially in vivo applications. Hence, there have been many attempts to tailor make the process.

Aniruddha S. Deshpande et al; Nanoscale res. lett.; 2008, 3, 221-229; synthesized Sulphur nanoparticles with an average size of 10 nm using the oil phase and 15 (vol. %) aqueous phase contains iron chelate and the $H_2S$ gas was used as a precursor.

Jun Lin et al; materials letters; 2001, 49, 282-286; synthesized AuNP using 0.056 M HAuCl4 and 0.32 M $NaBH_4$ using CTAB/octane reverse micelle and stabilized with dodecanethiol resulted in the formation of 1D, 2D and 3D superstructures.

Even after continuous research there are long standing problems limiting the full utilization of AuNC's like uniform size clusters, their thermo dynamical stability as clusters are having the tendency to grow further. Moreover, once the clusters reach to critical size they formed supercritical nucleus and grow further until the growth is arrested by capping agent. Once they form the supercritical nucleus they loose the property of luminescence and surface plasmon is dominated. Another difficulty is water soluble and isolable nanocrystals/nanoparticles (Kyosti Kontturi et al; ChemPhysChem; 2006, 7, 2143-2149). We have overcome both the hurdles; the 10-22 nm globular aggregates stabilized with amine group of hydrazine hydrate or dicarboxyacetone of citric acid or capped with mercaptopropionic acid or MUDA can be easily extracted by centrifugation and re-dispersed in water. Stability at low pH is desirable for drug delivery especially AuNP's capped with MUDA, mercaptoundeconic acid which in general are stable only in highly basic pH 9-13. Huan-Tsung Chang (Anl. Chem. 2008, 80, 1497-1504) showed stabilization at low pH by reducing tempt. to 4° and storing in dark; is again a limitation. The stability at low pH 3.5 MUDA capped 10-22 nm globular nano aggregates has the potential to replace the toxic PEG/bifunctional PEG (high cost) which at presently used for the drug delivery and many other bio-applications, also shows some form of toxicity. (Xiao-Dong Zhang et al). The 10-22 nm globular aggregates can be used dynamically in various bio applications including drug delivery.

These problems make the use of gold nanocrystals/nano dots restrictive in biological systems, especially for in vivo applications. Further, according to some studies Ramsay D L, Arch Dermatol. 1992 July; 128(7):931-3 possible protective role for UV-β therapy has been suggested in case of cutaneous T-cell lymphoma and immuno-regulatory. UV-β irradiating in geriatric patients increase the level of 25-hydroxyvitamin D levels (B. L. Diffy, Phys. Med. Biol.; 1980, V. 25 (3), 405-426). UV-β therapy was also used for skin disorders like lupus and sepsis; against infection of antibiotics resistance strains etc (Dr. Jonathan V. Wright: Harnessing the healing power of light Part 1). In such cases also role of desirable size of AuNP's/AuNC's or AgNP/AgNC's with selective UV-β luminescence is contemplated wherein it may be applied locally on the affected area.

Hence, there is a long standing need of prior art of AuNC's of controlled aggregate of 10 nm to 22 nm size which are biocompatible, non-toxic, capable of UV-β and visible emissions which may be used dynamically for various biomedical applications like UV and, phototherapy, drug delivery, biosensing, bio-labelling/bioimaging applications simultaneously. Also, the fluorescence remains unchanged in solid state for both as synthesized amine/DCA capped as well as after capping with MUDA/MPA.

The emission energy decreases with increasing number of atoms. The inventor has attempted to overcome the limitations of prior art and disclosed narrow size distributed, photo stable, multicolour fluorescence and capped globular nano aggregates (of size 10-22 nm) made up of 2-6 atoms ultra small clusters (encapsulated in a matrix of amine/dicarboxyacetone) with the functional group amine or carboxyl extractable and dispersed in water; capable of UV emission at 300-335 nm+/−5 nm; visible emissions: green emission when blue/green filter was used and 590-650 nm $2^{nd}$ order red emission; no plasmon resonance at 500-550 nm. These 10-22 nm size aggregates of atomic quantum ultra small nanoclusters which by virtue of the larger aggregate size (10-22) are safer than individual atomic nanoclusters/nanoparticles of 1-5 nm (Yu Pan, Willi Jahnen Dechent; Small, 2007, 3(11), 1941-1949), while at the same time retaining the optical properties of fluorescence which is the characteristics of atomic quantum 1-5 nm nanoclusters/nanoparticles (Beatriz Santiago Gonzalze et al: ACS Nanolett. 2010, 10, 4217-4221). Such aggregates can be the excellent fluorescent probe including for cell imaging both in vivo and in vitro, sensing and therapy. By virtue of the intense fluorescence which can replace the toxic semiconductor quantum dots etc.

OBJECTS OF THE INVENTION

The main object of the present invention is to provide nano aggregates of molecular nano clusters of noble metals and a process for the preparation thereof.

Another object of the present invention is to provide narrow size distributed, photo stable multicolour fluorescence, capped and spherical nano aggregates (size range of 10-22 nm) made up of 1-6 atoms stable clusters (embedded in amine/DCA) and also MUDA capped with UV emission at 300-335 nm and visible emission (green when use blue or green filter) red emission at 590-650 nm.

Another object of the present invention is to provide nano aggregates which are not showing the surface plasmon resonance which is the characteristic of ultra small clusters. Another object of the invention is to provide spherical nano aggregates (USMNCs) capped with mercaptoundecanoic Acid (MUDA) which are stable at pH 3-4 at RT (~25) and having 6 times enhanced fluorescent emission.

Yet another object of the invention is to provide a process for the preparation of nano aggregates which are non-toxic, biocompatible and surface can be modified by ligand exchange to append with MUDA or with another mercaptan ligand.

SUMMARY OF INVENTION

Accordingly, the present invention provides capped spherical nano aggregates of size 10-22 nm comprising molecular ultra small clusters of 1-6 atoms of noble metals selected from the group consisting of Au, Ag, Pt and Pd, and said clusters of 1-6 atoms being stabilized by a capping agent forming, d nano aggregates showing UV emission at 300-335 nm, no plasma resonance and visible $2^{nd}$ harmonic emission at 590-650 nm.

In one embodiment of the present invention, capping agent used is a mild reducing agent selected from the group consisting of hydrazine hydrate or citric acid in water.

In an embodiment of the present invention, the surface of nanoaggregates is stabilized and capped by amine or dicarboxyacetone (DCA) of a mild reducing agent along with the oxyethylene group.

In another embodiment of the present invention, mercapto undecanoic acid is used as a capping agent by ligand exchange of amine or dicarboxyacetone.

In another embodiment of the present invention, mercapto undecanoic acid capped nano aggregates are stable at pH 3-4 at room temperature ranging between 25-35° C.

Still in another embodiment of the present invention, mercapto undecanoic acid capped nano aggregates show 6 times more floresecence intensity in comparison to amine/dicarboxyacetone capped nano aggregates.

Still in another embodiment of the present invention, nanoagregates show green emmission when blue or green filters are used.

Still in another embodiment of the present invention, a process for the preparation of spherical nano aggregates, wherein the said process comprising the steps of;
 a) preparing a oil phase by stirring cyclohexane and non ionic surfactant Triton 100-X (C14H22O(C2H4O)n (n=9-10) in ratio ranging between 52:22 wt. % to 54:24 wt % for 11-12 hrs at room temperature ranging between 25-35° C. with constant stirring and adding 7-11 wt. % n hexanol into it and stirring further for 10-12 hrs at room temperature ranging between 25-35° C.;
 b) dividing oil phase as obtained in step (a) into two equal parts;
 c) adding aqueous solution of freshly prepared 0.056 M metal salt in one part of oil phase as obtained in step (b) and stirring for 10-12 hrs;
 d) adding aqueous solution of freshly prepared 0.32 M mild reducing agent in second part of oil phase as obtained in step (b) and stirring for 10-12 hrs;
 e) combining solution as prepared in step (c) into the solution as obtained in step (d) dropwise and further stirring the solution for a period ranging between 10-20 days at room temperature ranging between 25-35° C. to obtain solution containing nanoaggregates;
 f) centrifuging solution containing nanoaggregates as obtained in step (e) at 5000-6000 rpm for 10-20 min. at room temperature ranging between 25-35° C. and washing with water and ethyl alcohol 2-3 times to obtain spherical nano aggregates.

Still in another embodiment of the present invention mild reducing agent used in step (d) is selected from the group consisting of hydrazine hydrate or citric acid in water.

Still in another embodiment of the present invention metal salt used in step (c) is Auric Chloride, Silver nitrate and Platinum Chloride.

DETAILED DESCRIPTION OF THE INVENTION

"Gold nanoparticles/crystals" as used in the specification is with reference to definitions of Zheng et al in Nanoscale, 2012, 4, 4073

"Ligands" on the surface of nanocrystals clusters/nanoparticles, sometimes also called capping groups or surfactants, etc., are certain types of organic or bio molecules which also acts as spacer for unconstrained binding of targeted biomolecule or linker for further functionalization of biomolecule/polymer etc.

Figure 1:
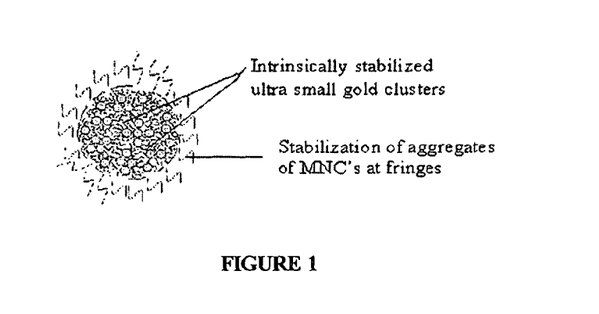
FIG. 1 shows a schematic representation of capped at fringes with amine or DCA along with oxyethylene group stabilizing the spherical nano aggregates of noble metal (Nb); consists of molecular ultra small nano clusters embedded in amine or DCA acting as a steric hindrance for further growth and stabilizing the clusters kinetically (nano aggregates of MUSNbNC).

The present invention describes the 10-22 nm capped globular aggregates of molecular ultra small clusters of 1-6 atoms as in FIG. 1.

According to the object of the invention the aggregates are characterized in having UV emissions at 300-335 nm and also have visible emissions: green when excited with blue and green filter and 590-650 nm $2^{nd}$ harmonics emission.

In accordance to the objects of the current invention the gold aggregates have no plasma resonance.

Further in accordance to the objects of the current invention spherical nano aggregates (MUSAuNC) capped with MUDA are stable at pH 3-4 and having six times higher emission as compared with amine/dicarboxyacetone capped.

In the current invention the Au aggregates are biocompatible and usable for biosensing, bioimaging, biomarker, Fluorescent Marker, UV & photo therapy and drug delivery both in vivo and in vitro applications.

In the current invention the MUDA capped by ligand exchange reaction of nano aggregates (of MUSAuNC) formed by Reverse Micro Emulsion Method as detailed below:

Oil phase: The reverse emulsion consists of cyclohexane, Triton 100X as surfactant and n hexnol as co-surfactant is prepared and split into two parts, RM 1 and RM 2.
Water phase: Consists of precursor, i.e. auric chloride (A) and reducing agent-hydrazine hydrate (HH) or Citric Acid (CA) or sodium borohydrate (B).

To RM1, A precursor is added and mixed well and to RM 2 part B reducing agent is added and mixed well. This is followed by mixing parts A to B drop wise at RT (~25 deg C) with constant stirring. These results initially in formation of discrete Au/Ag, Pt ultra small NC (crystalline nanocluster) below 1 nm and having 1-6 atoms stabilized with amine of hydrazine hydrate or dicarboxyacetone (DCA) of citric acid because of slow inter droplet exchange. By virtue of presence of n-hexanol these MUSNbNC's are further agglomerated to the water droplet size of reverse micelle and further stabilized at fringes again with amine or DCA along with oxyethylene group of triton 100X.

The optico-physico-chemical properties of Au/Ag/Pt NC's are characterized with various characterization techniques viz. UV-Absorption; Single Photon Fluorescence Spectroscopy; Photoluminescence spectroscopy, PL; Transmission Electron Microscope (TEM) and HRTEM, X-ray Photoelectron Spectrometer, Infra-red Fourier transform technique, Zeta potential and Mass Analysis.

The particles synthesized using reverse microemulsion technique and using mild reducing agent like hydrazine hydrate and citric acid results in the formation of 10-22 nm spherical nano aggregates of molecular ultra small nanocrystals of noble metals like Au, Ag and Pt. The controlled size and shape of 10-22 nm nano aggregates with intense and multicolour (UV, green and red) fluorescence has wide range of potential applications in bio imaging for both in vitro and vivo applications. The quantum efficiency of Au nano aggregates reduced with hydrazine hydrate was 0.37 and 4.92 when reduced with citric acid. The calculations are made using the comparative method using rhodoamine B as a reference and by keeping the absorbance constant.

$$QE_S = \frac{I_S \times QE_R}{I_R}$$

Where, $QE_S$: Quantum efficiency of sample
$I_S$: Intensity of sample (359.81, Au nanoaggregate reduced with HH (0.08) and 1000 Au nano aggregate reduced with CA, 0.017)
$QE_R$: Quantum efficiency of reference (rhodamine B, 0.65)
$I_R$: Intensity of reference (620.65 at 0.08 and 131.88 at 0.017)

The particles synthesized using reverse microemulsion technique and strong reducing agent like sodium borohydrate; though the nano aggregates are made up of molecular ultra small nanocrystals; shows good fluorescent, there was no control over size & shape and hence cannot be used in any kind of applications. On the contrary the aqueous synthesis shows better range of size distribution i.e. 1-20 nm and also the flower like particles in the range of 20-250 nm. For utilization in particular application the particles and the flowers should be separated which is difficult task. Also the particles synthesized in aqueous phase either reduced with sodium borohydrate or hydrazine hydrate are amorphous and cannot be sediment and separated by centrifugation and the un reacted precursor and reducing agent remain the part of the solution that may interfere and cause some kind of toxicity in case of bio applications. The 1-5 nm by product of aqueous synthesis using the hydrazine hydrate as a reducing agent cannot be used in vivo applications as in long term usage 5 nm particles may accumulate in liver which can be a reason for toxicity and therefore they cannot be used for vivo applications and drug delivery. As they are not able to separate out from the reaction solution containing un-reacted precursor and reducing agent make them further unusable for drug delivery.

The MUDA capped nano aggregates of MUSAuNC's shows the stability in acidic pH. 3.5 and the fluorescence intensity was increased by six times. The MUDA capped nano aggregates of MUSAuNC's can be easily replaced with the toxic and high cost bi-functional PEG. The nano aggregates synthesized with reverse microemulsion techniques and decorated with amine/carboxyl group and also the MUDA capped by ligand exchange reaction has the potential applications as a fluorescent marker. Fluorescent biochip, various bioimaging techniques both in vivo & vitro applications, biomedical applications like drug delivery, therapy, UV & photo therapy and also simultaneously can also be used for EM labelling.

The particles are tuned to emit green and red emission by varying the capping agent. Nano rod show much higher toxicity as compared to the spherical particles. This synthesis route renders the fabrication of nano aggregates of MUSNbNC's with multiple emissions UV, red and green just by using the various excitation filters irrespective of the capping agent and being spherical and in the range of 10-22 nm they are biocompatible and flush out of body and easy cellular uptake due to low friction.

The particles are extracted and can be stored in powder form and therefore can be utilized in many electronics applications also.

Following examples are given by way of illustration therefore should not be construed to limit the scope of the invention.

EXAMPLES

Example 1

Synthesis of Spherical Nano Aggregates of Molecular Ultra Small Gold Nano Clusters (MUSNC's) Using Hydrazine Hydrate (HH) as a Mild Reducing Agent and Reverse Microemulsion Technique Cyclohexane ($C_6H_{12}$) and non ionic surfactant Triton 100-X ($C_{14}H_{22}O(C_2H_4O)_n$ (n=9-10) in 52:22 wt. % were mixed in a RB flask while continuous stirring at room temperature (25° C.) for 12 hrs and n-Hexanol ($C_6H_{14}O$) in 11 wt % was added into it and further stirred for 12 hrs to obtained oil phase. The oil phase was divided in two flasks. In flask-1 aqueous solution of 0.056 M of Gold Chloride was added into oil phase while stirring continuously for 12 hrs and in flask-2 (0.32 M) of Hydrazine Hydrate solution was added into oil phase while stirring continuously for 12 hrs. After that in flask 2, the solution of flask 1 is added drop by drop and stirred continuously for 10 days. The complete reaction is carried out at room temperature (~25° C.).

| Preparation of reverse micro emulsion (RM):- unit weight % | | |
|---|---|---|
| 1. Cyclohexane- | 52 gm | } Stirring continuously on magnetic stirrer overnight, 12 Hrs |
| 2. Triton-100x | 22 gm | |
| 3. n-Hexanol | 11 gm | |
| Total: | 85 gm (85 Weight %) | |

RM Divided Equally into Two

Reverse Microemulsion Part 1 (RW part 1)   Reverse Microemulsion Part 2 (RW part 2)

Preparation of Aqueous Phase:
Total 15 ml (volume %), 0.056 M of Auric Chloride prepared freshly
1. Aqueous phase 1: In 7.5 ml of distilled water 0.056 M of Auric Chloride is dissolved
2. Aqueous phase 2: In 7.5 ml of distilled water 3.2 M of Hydrazine Hydrate is dissolved

| | | |
|---|---|---|
| In RM Part 1: | 7.5 ml of 0.056M of aqueous solution of Auric Chloride is added | } While stirring continuously on magnetic stirrer overnight or for minimum of 12 hours |
| In RM Part 2: | 7.5 ml 0.32M of aqueous solution of Hydrazine Hydrate is added | } While stirring continuously on magnetic stirrer overnight or for minimum of 12 hours |

After 12 hours, in RM Part 2 (Solution of Hydrazine Hydrate) and in RM Part 1 (solution of Auric Chloride) is added drop by drop and allowed to react for minimum of 10-15 days.

Extraction of Nano Aggregates of USMAuNC's:
The reaction solution containing nanoparticles is transferred in microcentrifuge tube (1.5 ml) and Centrifuge it at 5000-6000 RPM for 15 min. The supernatant is decanted and re-dissolve the precipitate in Distilled water. The particles are allowed to re-dispersed using cyclomixer (90 sec) and then with sonicator for 30 min till the complete dispersion of pellet; then again centrifuge it for 15 min's to settle down the particles and the pellet is dissolved in ethyl alcohol and the particles are again re-dispersed using cyclomixer and sonicator. The cycle is repeated twice again to remove the oil phase and surfactant completely. The Au nano aggregates are finally transferred in distilled water.

Characterization Details
UV Absorption:
The UV-visible spectra were acquired and recorded using Varian Make 'Carry WinUV'. The grating bandwidth was of 5 nm and xenon lamp used as a light source. The slit width was of 5 nm and water dispersed nano aggregates of Au NC's was scan for 200-800 nm range. The absorption peak of as synthesized Au nano cluster aggregates were observed at 223 and 278 nm as in FIG. 2 (*a*). The 520 nm surface plasmon peak was absent.

Fluorescence Spectroscopy:
The fluorescence spectroscopy was carried out using the Varian make PL and "ISS" make Photon Counting Steady State Fluorescence Spectrophotometer; with 300 W Xe lamp. Both excitation and emission slit width was kept at 1 nm. The samples were excited from 200 to 450 nm, at 230 nm excitation the peak maxima was observed at 305 nm and 591 nm as in FIG. 2 (*b*).

Figure 3:
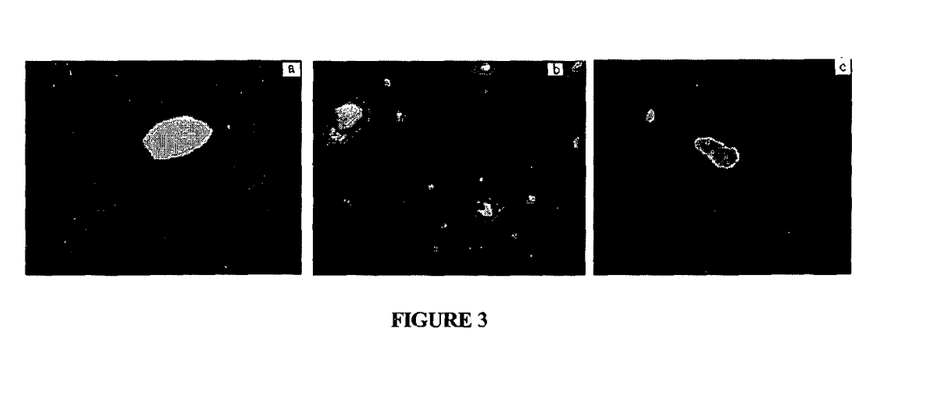
FIG. 3 shows fluorescence microscopy of Nano aggregate of MUSAuNC's reduced with HH a) UV filter b) Green filter c) Red filter

Fluorescence Microscopy:
To visualize the fluorescence in optical microscope the samples were prepared by making the thick film on the glass slide and air dried. The fluorescence was observed under Meiji Techno make MT6000 optical fluorescence microscope using UV, green and red filter as in FIG. 3.

Figure 4:
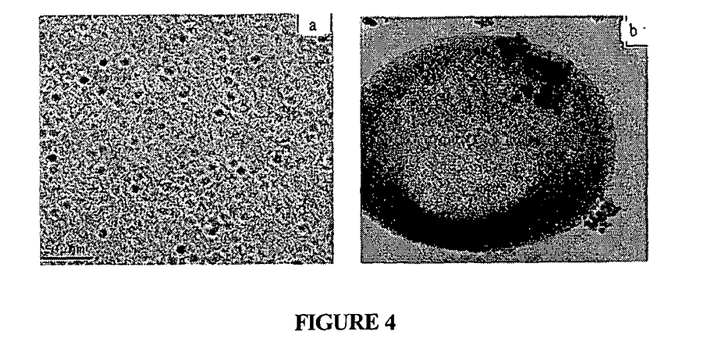
FIG. 4 shows HRTEM/TEM of nano aggregate of MUSAuNC's reduced with HH (a) HRTEM, after $1^{st}$ wash; morphology high mag. (b) core microemulsion droplet containing coalescent droplets and particles inside it; TEM low mag.
Figure 5:
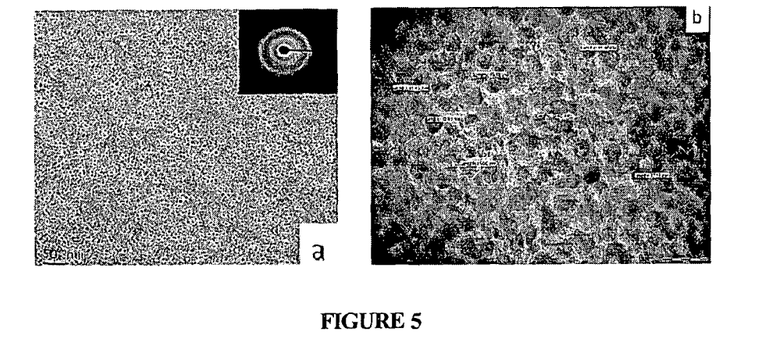
FIG. 5 shows HRTEM/TEM of Nano aggregate of MUSAuNC's reduced with HH, (a) Morphology (HRTEM), low magnification with crystalline diffraction rings; (b) high magnification of core microemulsion droplet containing coalescent droplets and particles therein; TEM.

Morphological Study:
The morphological features and size distribution of as synthesized Au NC's are measured with Carl Zeiss Make LIBRA 120, at 120 kV and at HRTEM 300 kV accelerating voltage. The samples were prepared by drop casting the water dispersed sonicated solution of particles onto the carbon coated copper grid. After air drying the samples are analyzed under TEM/HRTEM. The study shows the uniform, spherical, average size of 10-22 nm; more precisely 12-17 nm and narrow size distribution. The electron diffraction pattern (ED) shows the crystalline sharp rings as in FIGS. 4 & 5.

Mass Spectroscopy:

The MALDI samples were prepared by using DHB (2, 5 hydroxy benzoic acid) in 50% ACN and 0.1% TFA as a matrix. The mass analysis is carried out with AB Sciex Make Voyager-DE-STR MALDI-TOF using linear positive mode and ionization of Au crystals are carried out with 337 nm nitrogen laser. The mass spectra were accumulated for the 50-100 shots for each spectrum at 20 Kv. The MALDI Analysis shows 1-6 Au Atoms on which the various species of amine group like NH, NH2, and NH3 are adsorbed. The MALDI data is a representation of the polymer like structure consisting of ultra small clusters surrounded by the various species of amine group as in FIG. 6($a$); there is very little change in the peaks of 6 months stored sample FIG. 6($b$). The assignments of mass analysis peaks as in FIG. 6 ($a$) are given below:

TABLE 1

Figure 6:
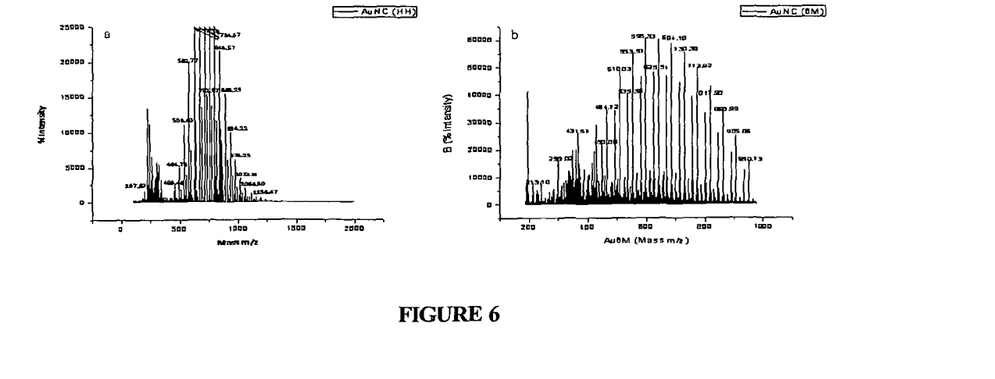
FIG. 6 shows mass analysis of nano aggregate of MUSAuNC's reduced with HH (a) freshly extracted (b) after 6 months storage in emulsion.

Nano aggregate of MUSAuNC's reduced with HH; peak assignments of MALDI Analysis, FIG. 6 (a)

| S. No. | Peak Positions | Assignments |
|---|---|---|
| 1. | 197.90 | $Au_1$ |
| 2. | 459.48 | $Au_2$—$(NH_2)_4$ |
| 3. | 494.75 | $Au_2$—$(NH2)_2$—$(NH_3)_4$ |
| 4. | 536.40 | $Au_2$—$(NH)_3$—$(NH_2)_6$ |
| 5. | 582.77 | $Au_2$—$(NH_2)_{11}$ |
| 6. | 714.61 | $Au_3$—$(NH)6$—$(NH_2)_2$ |
| 7. | 732.17 | $Au_3$—$(NH)_{16}$ |
| 8. | 888.23 | $Au_4$—$(NH2)_3$—$(NH_3)_3$ |
| 9. | 976.25 | $Au_4$—$(NH)_5$—$(NH_2)_7$ |
| 10. | 1066.50 | $Au_5$—$(NH2)_5$ |
| 11. | 1156.47 | $Au_5$—$(NH)_6$—$(NH_2)_5$ |

Figure 7:
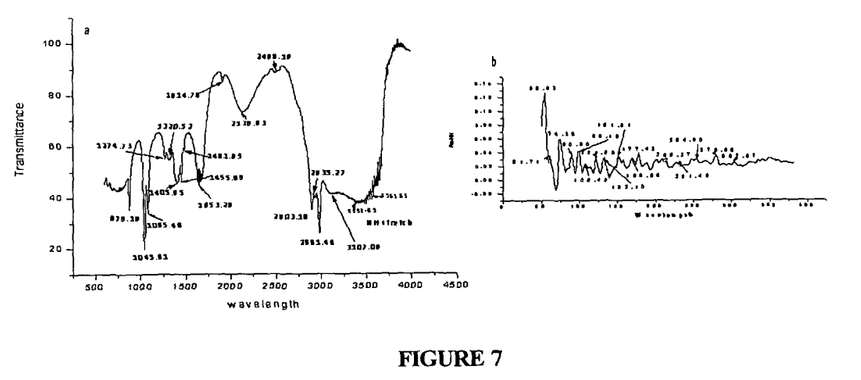
FIG. 7 shows FTIR spectra of Nano aggregate of MUSAuNC's reduced HH (a) MidIR (b) FarIR.

Fourier Transform Infrared Analysis, FTIR:

FTIR spectra in the region of 4000 to 600 $cm^{-1}$ were recorded with PerkinElmer Make Spectrum GX FTIR. One drop of suspended AuNC's in alcohol solution are dispersed and put onto the NACL crystal window and the peak positions of spectra were recorded and are their respective assignments are summarized in table 2, FIG. 7($a$).

Far IR:

The Far IR (ATR) analysis is carried out on Thermo-Nicolet make FTIR, 870 nexus using polyethylene detector. The most peaks are observed between 55-177 $cm^{-1}$ which is related to the ultra small gold crystals: Au—Au vibrations and the attach carbon (Janet Petroski, Mei Chou, Carol Creutz; J. of Organometallic chemistry 2009, 694, 1138-1143); 7(b)

TABLE 2

Assignments of FTIR peak; FIG. 7(a)

| Frequency Wavenumber ($cm^{-1}$) | Assignments |
|---|---|
| 879.19 | O—H bend |
| 1045.81 | Cyclohexane ring vibration |
| 1085.46 | Cyclohexane ring vibration |
| 1274.73 | C—C vibrations; C—H bend |
| 1320.52 | C—O stresch |
| 1405.95 | C—H bend |
| 1455.99 | C—H bend |
| 1653.29 | NH bend/Aromatic combination band |
| 1914.78 | Aromatic combination band |
| 2139.93 | C—O; C=C |
| 2903.18 | C—H stretching |

TABLE 2-continued

Assignments of FTIR peak; FIG. 7(a)

| Frequency Wavenumber ($cm^{-1}$) | Assignments |
|---|---|
| 2935.27 | C—H stretching asymmetric |
| 3392.65 | NH stretch |
| 3361.63 | NH stretch |

Figure 8:
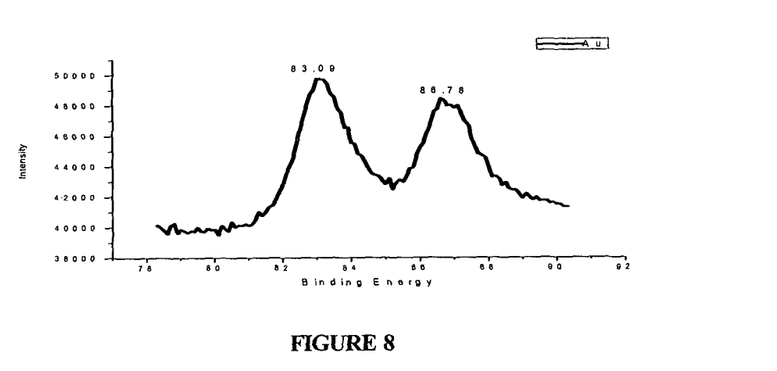
FIG. 8 shows XPS spectra of Nano aggregate of MUSAuNC's reduced with HH.

X-ray Photo Spectroscopy, XPS:

A thin film is formed onto the silicon wafer, air dried and analyzed with VG Scientific Ltd., UK Make ESCA-3000 with a base pressure of $1.0 \times 10^{-9}$ Pa. and Mg K$\alpha$ radiation as an X-ray source operated at 150 W. The XPS analysis confirms the oxidation state of gold is zero, $Au^0$. The Au bands of as synthesized MAuNC's are at 83.09 and 86.85 as in FIG. 8 from 4f 7/2 and 4f 5/2 shell with a difference of 3.76 eV between the peaks, thus represents the zero valence of gold.

Zeta Potential:

By conducting the 10 runs and 5 cycles for each run; the mean electrostatic potential of as synthesized Au NC's is −31.8 which back up the good stability Example 2

Synthesis of Gold Nano Aggregates of MUSNC's Using Citric Acid (CA) as a Mild Reducing Agent and Reverse Microemulsion Technique The synthesis procedure is same as mentioned in example 1, except in aqueous phase 0.32 M Citric Acid was used instead of 0.32 M Hydrazine Hydrate.

Figure 9:
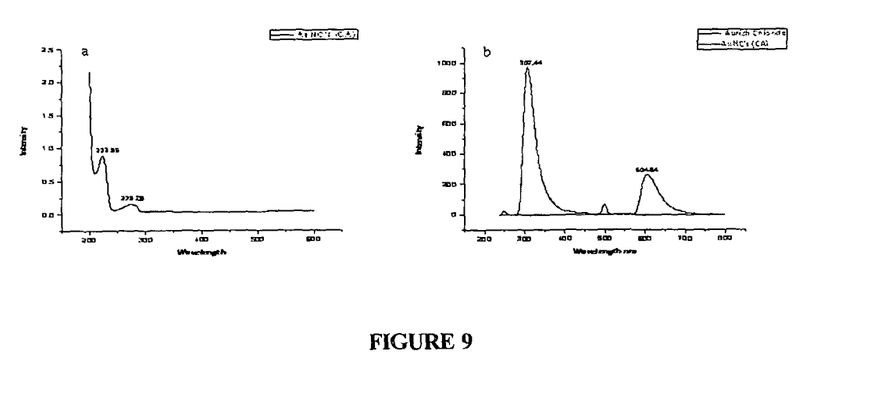
FIG. 9 shows spectroscopy of Nano aggregate of MUSAuNC's reduced with citric acid (CA) (a) UV-absorption (b) Photoluminescence spectra (excitation at 290 nm).

UV Absorption:

The optical properties are similar as observed in example 1. The absorption peak of nano aggregates was observed at 223 and 277 nm as in FIG. 9 ($a$); the surface plasmon peak was absent.

Photoluminescence Spectroscopy:

The fluorescence spectroscopy is carried out using the Varian make PL. The excitation slit was kept at 2.5 nm and emission slit width was kept at 5 nm. The samples were excited from 200 to 450 nm, at 250 nm excitation the peak maxima was observed at 307 nm and 605 nm with an shift of 2 nm and 6 nm respectively as in FIG. 9 ($b$)

Figure 10:
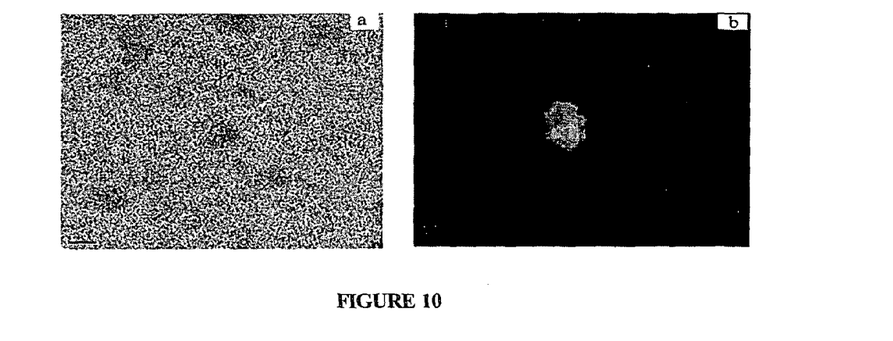
FIG. 10 shows HRTEM and Fluorescence Microscopy of Nano aggregate of MUSAuNC's reduced with CA (a) Morphology (b) Fluorescence with Carl Zeiss Bio AFM using blue filter.

The fluorescence was observed under Carl Zeiss BioAFM optical fluorescence microscope using Blue filter as in FIG. 10($b$).

Morphological Study:

The morphological features and size distribution of gold nano aggregates of USMAuNC's are observed and measured under HRTEM; the size, shape and distribution are similar as observed in example 1; i.e. spherical 10-22 nm uniformly dispersed as in FIG. 10($a$).

Example 3

Synthesis of Silver Nano-Aggregates of MUSNC Reduced with Mild Reducing Agent Hydrazine Hydrate and Reverse Microemulsion Technique The synthesis procedure is same as mentioned in Example 1, except in aqueous phase 0.056 M of precursor silver nitrate is used instead of auric chloride.

Figure 11:
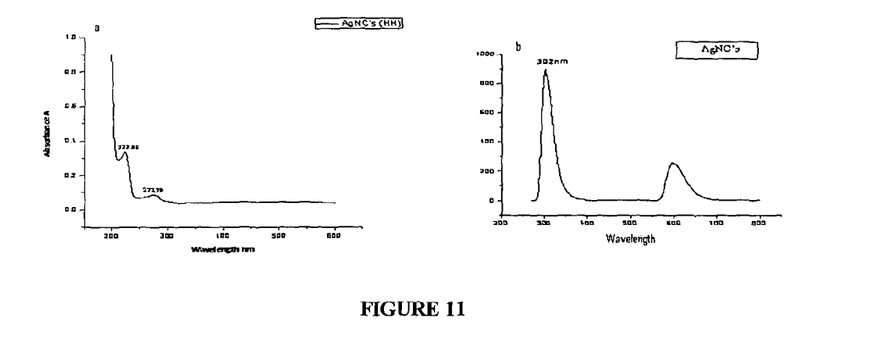
FIG. 11 shows spectroscopy of Nano aggregates of MUSAgNC's reduced with HH: (a) UV-absorption (b) Photoluminescence spectra.
Figure 12:
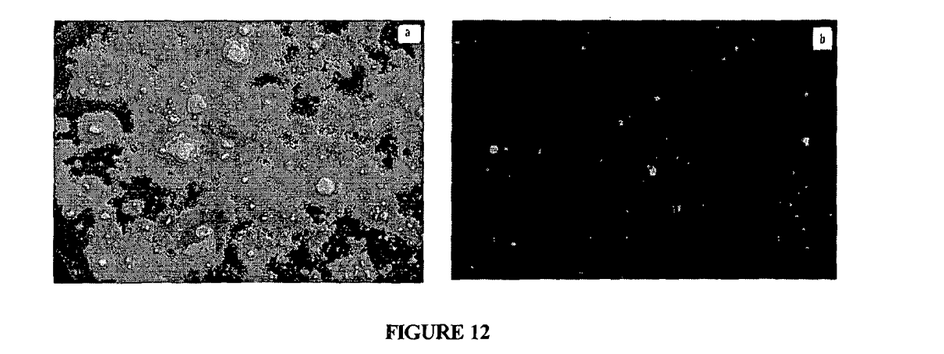
FIG. 12 shows Fluorescence Microscopy of Nano aggregates of MUSAgNC's reduced with HH (a) Green and (b) Red filter.

The optical properties are similar as observed in Example 1 and 2, the absorption peaks were observed at near 222 nm and 277 nm, as in FIG. 11 ($a$) with same instrument parameters as mentioned in Example 1 and fluorescence emission is at 302 nm and 600 nm as in FIG. 11 (b) analyzed with varian make PL with same instrumentation parameters as mentioned in Example 2. It shows the green and red emission using green and red filter under optical fluorescence microscope as in FIG. 12.

Figure 13:
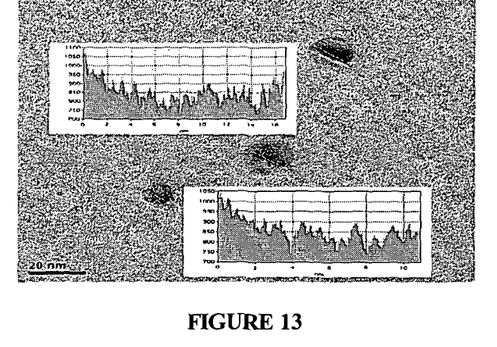
FIG. 13 shows HRTEM of Nano aggregates of MUSAgNC's reduced with HH (a) high mag. Morphology, size and shape.
Figure 14:
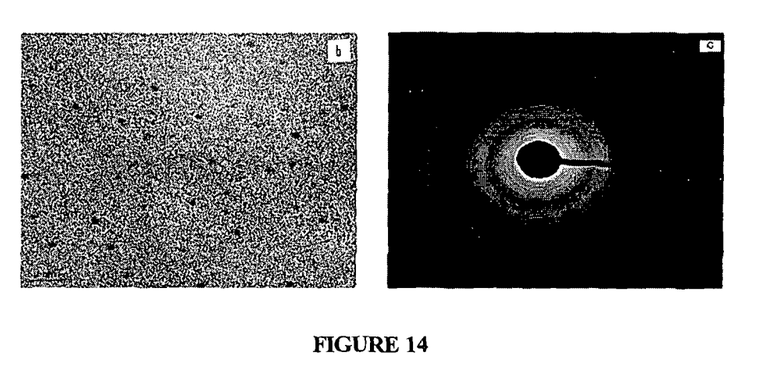
FIG. 14 shows TEM of Nano aggregates of MUSAgNC's reduced with HH (b) low mag. size distribution (c) diffraction.

The TEM and HRTEM analysis shows 10-22 nm spherical crystalline clusters with narrow size distribution of nano aggregates, as in FIGS. 13 & 14.

Figure 15:
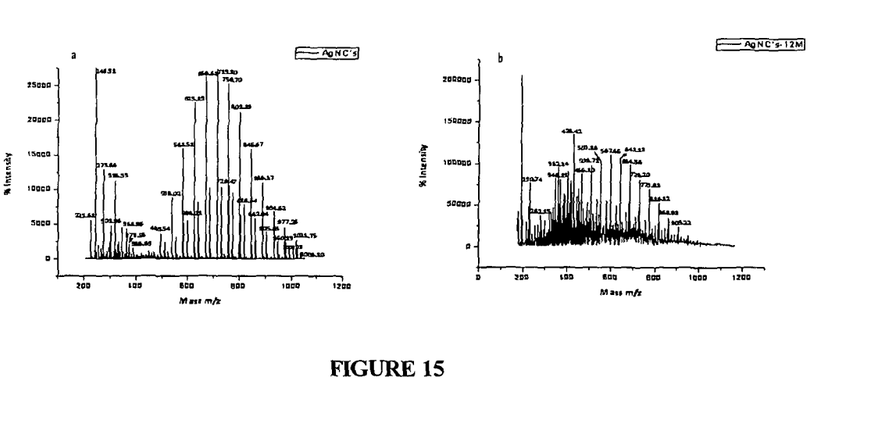
FIG. 15 shows mass analysis of Nano aggregates MUSAgNC's reduced with HH, (a) freshly prepared (b) after 12 months of storage.

The mass analysis shows the clusters of 1-10 atoms decorated with amine group, as in FIG. 15. It shows slightly more atoms as compared in case of Au atoms. In case of Au atoms are restricted to 1-5 or maximum of 7 atoms where as in case of Ag nano particles the clusters are slightly bigger i.e. 1-10 atoms maximum of 12-14 atoms decorated with $NH/NH_2/NH_3$ molecules on the surface. The increase in number of atoms in case of Silver nano crystals might be due to small mass or atomic radii as compared with gold. There was not much change in the spectra of freshly prepared and after storing the particles in emulsion for 12 months (FIG. 15).

Example 4

Synthesis of Platinum Nano-Aggregates of MUSNC Reduced with Mild Reducing Agent Hydrazine Hydrate and Reverse Microemulsion Technique The synthesis procedure is same as mentioned in Example 1, except in aqueous phase 0.056 M of precursor platinum chloride was used.

Figure 16:
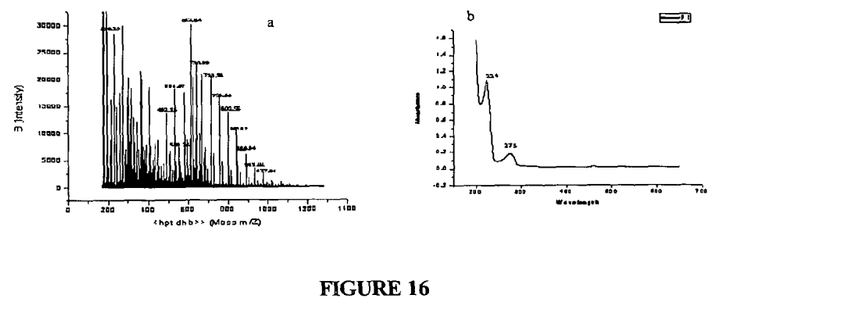
FIG. 16 shows mass and UV analysis of Nano aggregates of MUSPtNC's reduced with HH (a) Mass spectra (b) UV-absorbance spectra.
Figure 17:
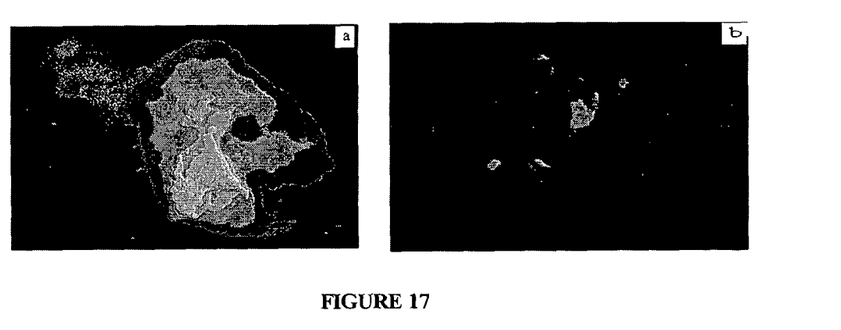
FIG. 17 shows Fluorescence Microscopy of Nano aggregates of MUSPtNC's reduced with HH (a) green filter (b) Red filter.
Figure 18:
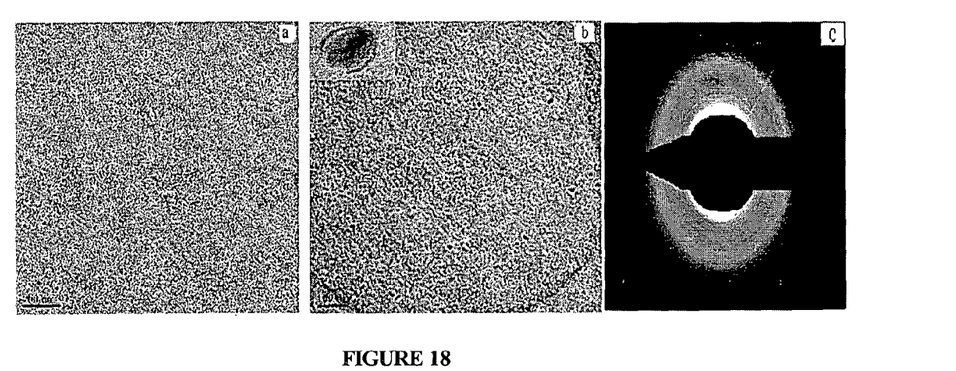
FIG. 18 shows HRTEM of Nano aggregates of MUSPt-NC's reduced with HH (a & b) morophology; shape and size distribution (C) diffraction.

The optical and morphological features and mass analysis results are similar as observed in example 1, 2 and 3 as indicated in FIGS. 16, 17 and 18.

Example 5

Synthesis of Gold Nano-Aggregates of MUSNC Reduced with Strong Reducing Agent Sodium Borohydrate (NaBH4) and Reverse Microemulsion Technique The synthesis procedure, instrumentation and sample preparation techniques was same as mentioned in Example 1, except in aqueous phase 0.32 M of sodium borohydrate was used as a reducing agent instead of hydrazine hydrate.

Figure 19:
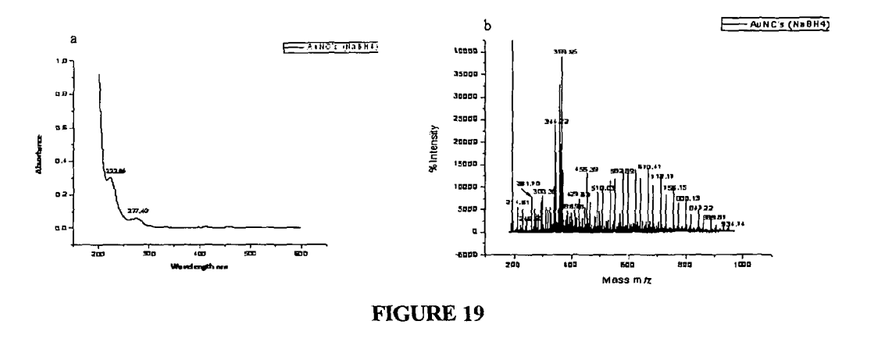
FIG. 19 shows UV absorption and Mass analysis of Nano aggregates MUSAuNC reduced with Reduced with Sodium Borohydrate ($NaBh_4$) (a) UV-absorption spectra (b) Mass spectra.
Figure 20:
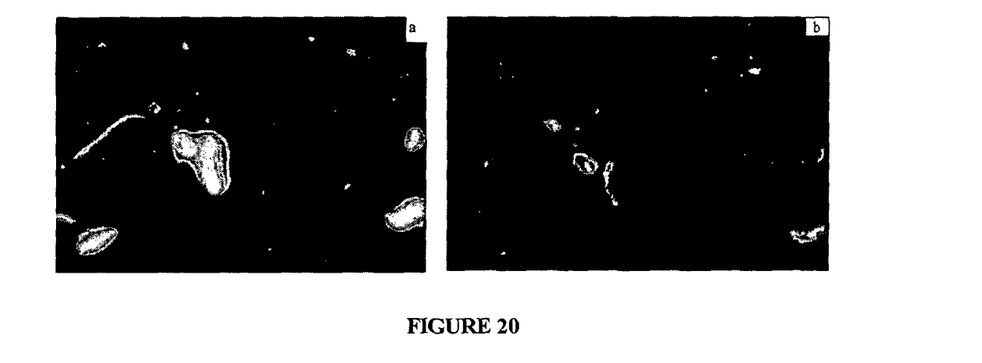
FIG. 20 shows Fluorescence Microscopy of Nano aggregates MUSAuNC Reduced with $NaBH_4$ (a) UV and (b) Red filter.
Figure 21:
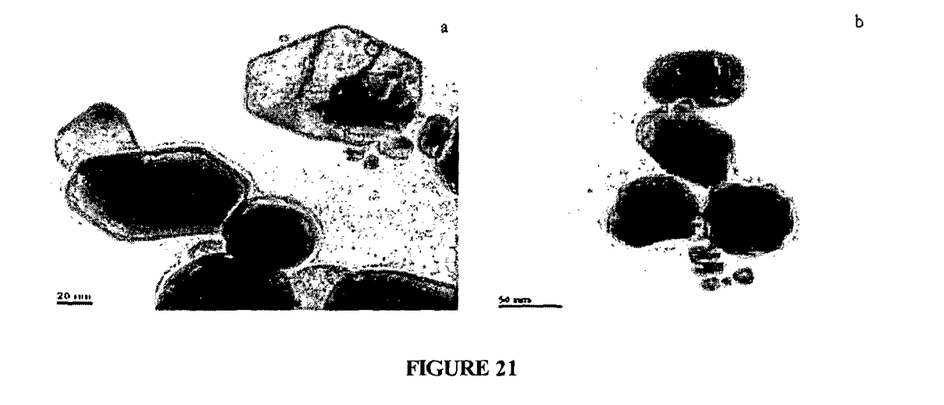
FIG. 21 shows HRTEM of Aqueous Synthesis of gold nanoparticles reduced with NaBH4; (a)&(b) Morphology: size and shape.

The UV analysis results were similar as observed in Example 1-4. The absorption peaks of nano aggregates were observed at 223 and 277 nm as in FIG. 19(a); the surface plasmon peak was absent. The fluorescence was observed under Miji Fluorescence optical Microscope using UV and Red filter as in FIG. 20. The HRTEM analysis shows that there is no control on size and shape. The particles are spherical, triangles and hexagonal etc and the size range is 1-250 nm, very wide range of size distribution; FIG. 21. The mass analysis shows very similar results observed in Examples 1-4; as in FIG. 19 (b).

Example 6

Aqueous Synthesis of Gold Nano Nanoparticles Reduced with Strong Reducing Agent Sodium Borohydrate (NaBH4) while Continuous Stirring In RB flask-1, 0.056 M of Auric Chloride is dissolved in 10 ml of Millipore water and stirred for 12 hrs on magnetic stirrer. In RB flask-2 (0.32 M) of sodium borohydrate is dissolved in 10 ml of distilled water and stirred for 12 hrs. Next day 0.056 M of aqueous solution of RB flask-1, Auric Chloride is added drop by drop into the in RB Flask-2 containing 0.32 M of aqueous solution of sodium borohydrate. It forms the black precipitate, the reaction is carried out for 3-5 days and particles are characterized using the same instrumentation and sample preparation methods as described in Example 1.

Figure 22:
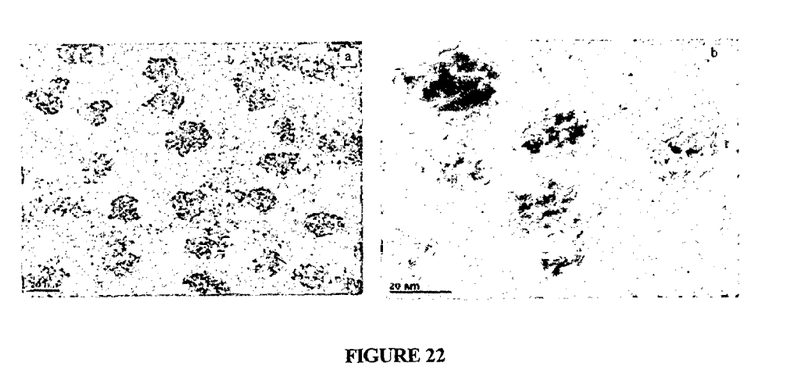
FIG. 22 shows HRTEM of Aqueous Synthesis of nano aggregates of USMAuNC reduced with NaBH4 Morphology (a) low mag. (b) high mag.

The particles do not show fluorescence and the HRTEM analysis (FIG. 22) shows particles in the range of 1-20 nm and flower like structure in the range of 20-250 nm. The particles can not be extracted by centrifugation and the unreacted precursor and reducing agent remained the part of colloidal solutions.

Example 7

Aqueous Synthesis of Gold Nano Nanoparticles Reduced with Mild Reducing Agent Hydrazine Hydrate (HH) while Continuous Stirring The synthesis, instrumentation and sample preparation methodology was same as mentioned in example 6, except 0.32 M Hydrazine Hydrate was used instead of sodium borohydrate. It forms the black precipitate. The reaction was carried out till the dissolution of pellete.

Figure 23:
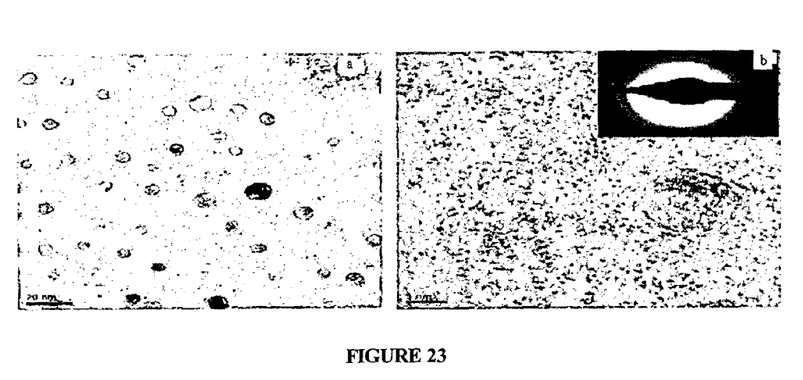
FIG. 23 shows HRTEM of Aqueous Synthesis of nano aggregates of MUSAuNC reduced with HH Morphology (a) low mag. (b) high mag.
Figure 24:
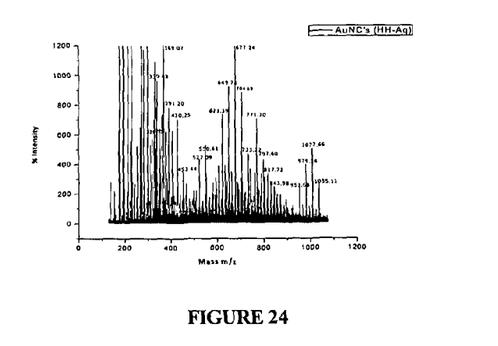
FIG. 24 shows mass spectra of Aqueous Synthesis of nano aggregates of MUSAuNC reduced with HH.

HRTEM analysis shows the narrow size distribution in the range of 1-5 nm and the particles are amorphous as in FIG. 23. The mass analysis shows the capping of amine groups (FIG. 24). As mentioned in Example 6, here also the particles can not be extracted by centrifugation and the unreacted precursor and reducing agent remained the part of colloidal solutions.

Example 8

Capping of MUSAuNC's by Ligand Exchange with Mercaptoundeconic Acid (MUDA)

MUSAuNC's was synthesized in example 1. (250 mg of) MUA was first dissolved in 5 ml water and 10 ml ethyl alcohol for 5 hour while continuous stirring on magnetic stirrer. This forms milky white solution. After 5 hours 10 ml of chloroform was added and stirred for 12 hrs then ~5 mg of MUSAuNC's dispersed in 5 ml of distilled water was added and allowed to react for 20 days. The exchange of ligand MUDA was checked with the help of zeta potential when complete negative charge on the MUSAuNC's was replaced by +ve charge of SH group (as in table 3). pH of synthesized with Hydrazine hydrate was 3 and pH after capping with MUDA was 3.5.

Figure 2:
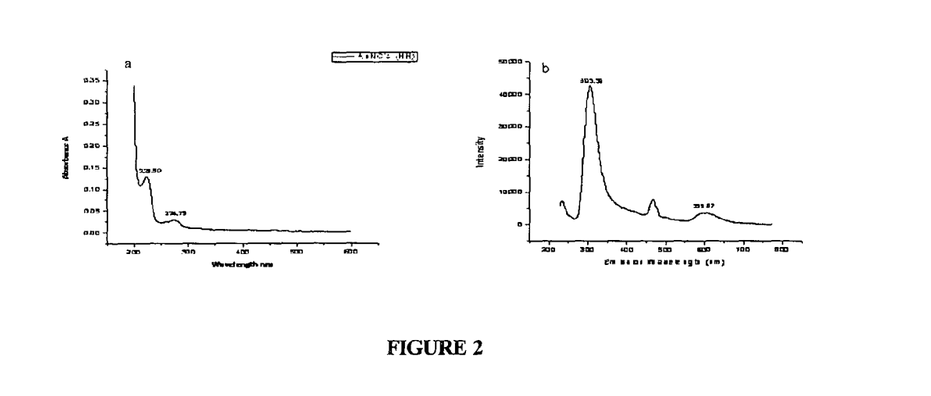
FIG. 2 shows spectroscopy of Nano aggregate of MUSAuNC's reduced with Hydrazine hydrate (HH) (a) UV-absorption spectra; (b) Florescence spectra; excitation at 230 nm.
Figure 25:
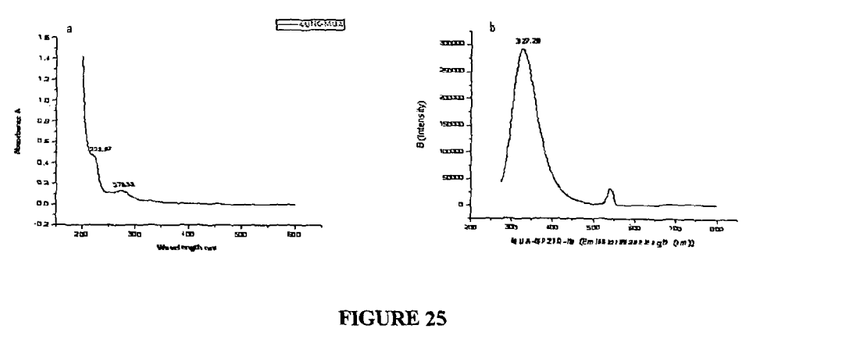
FIG. 25 shows spectroscopy of Nano aggregate of MUSAuNC's reduced with HH and capped with MUDA: (a) UV-absorbance spectra (b) Fluorescence spectra.
Figure 26:
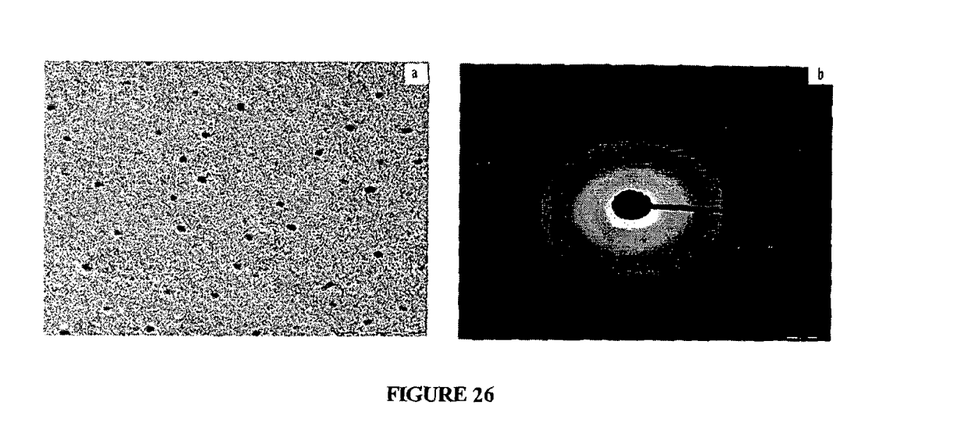
FIG. 26 shows TEM of Nano aggregate of MUSAuNC's reduced with HH and capped with MUDA: (a) Morphology (b) diffraction.

There was reduction in absorption intensity but no shift in absorbance wavelength as in FIG. 25(a), and the fluorescence intensity was increased six times as compared with FIG. 2 (b) which was near 45000 to 300000 as in FIG. 25(b). There was no change in morphology as observed in FIG. 26.

TABLE 3

Zeta potential of MUDA capped MUSAuNC's

| S. NO. | Zeta Potential (mV) MUDA dissolved in 50% Alcohol; 10 days reaction | Zeta Potential (mV) MUDA dissolved in 1:1:1 water:Alcohol:chloroform; 25 days reaction |
|---|---|---|
| 1. | −12.47 | 7.82 |
| 2. | −15.76 | 8.27 |
| 3. | −24.91 | −3.78 |
| 4. | −25.72 | 2.35 |
| 5. | −22.92 | 6.63 |
| Mean | −20.35 | 4.25 |

Example 9

Capping of MUSAuNC's by Legand Exchange with Mercaptopropionic Acid (MPA)

Figure 27:
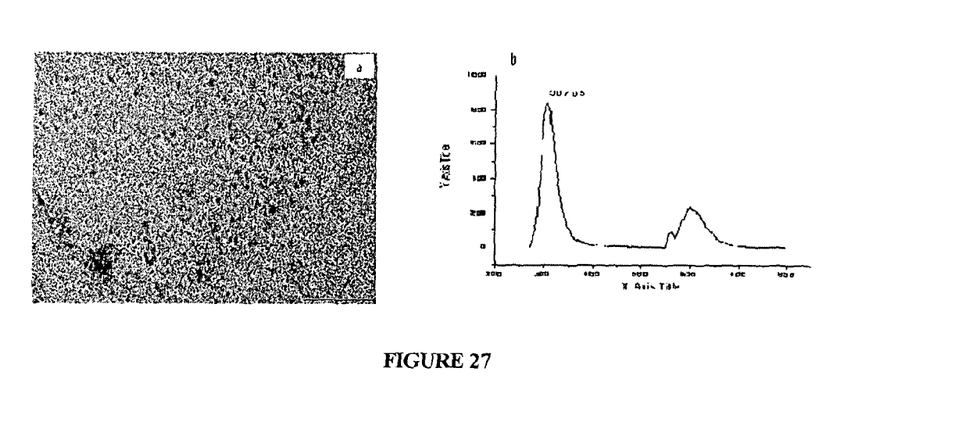
FIG. 27 shows TEM and PL analysis of Nano aggregate of MUSAuNC's reduced with HH and capped with MPA: (a) Morphology (b) Photoluminescence spectra.

MPA was dissolved in 5 ml of 50% of alcohol while continuously stirring, then in 5 ml water containing nano aggregates of MUSAuNC's was synthesized in example 1 was added and allowed to react for 4-8 days till the surface is completely replaced by MPA. The results were similar as observed in example 1. The mean Zeta potential of MPA capped MUSAuNC's was 14.47 mV (FIG. 27)

TABLE 4

Comparative table

| Reference | Nanoparticle/ nanocluster size | Capping | Fluorescence emission UV | Fluorescence emission Green | Fluorescence emission Red and near IR | Surface plasmon |
|---|---|---|---|---|---|---|
| Present invention | 10-22 nm capped Spherical Au nano aggregates | Amine Carboxyl Au nano aggregate are further capped with MPA & MUDA | 300-330 | Using blue and green filter | 590-620 | Absent |
|  | 10-22 nm capped Spherical Ag nano aggregates |  | 300-330 | Using blue and green filter | 590-620 | Absent |
|  | 10-22 nm capped Spherical Pt nano aggregates |  | 300-330 | Using blue and green filter | 590-620 | Absent |
| Beatriz Santiago Gonzalez et al; Nano let. 2010, 10, 4217-4221 | Clusters of $Au_2$ to $Au_{11}$ Size below 1 nm | PVP | 315-350 nm | 520 nm | Not shown | Absent |
| Walter H Chang etal; J. of Med. And Bioloical Engg., 2009, 29 (6), 276-283 and C. A. J Lin et al; ESBME-Peter | $Au_8$ | PAMAM | Blue emission | absent | absent | absent |
|  | AuNP-THPC | Replace with MUA | absent | Green emission | absent | Not shown |
|  | ~3.4 nm $Au_{25}$ | BSA | absent | absent | Red Emission | absent |
|  | 5.55 nm AuNP | absent | absent | absent | absent | 520-530 nm |
| Thalappail pradeep etal; Chemical Eur. J.; 2009, 15, 10110-10120 | $Au_{25}SG_{18}$ | absent | absent | absent | Near IR | absent |
| P. K. Jain et al, ACS, Accounts of chem. 1 Res. Dec. 2008, 41 (12), 1578-1586 | 10 nm Au nanospheres | absent | absent | absent | absent | 520 |
|  | 10 nm Ag Nanosphere | absent | absent | absent | absent | 390 |

ADVANTAGES OF THE INVENTION

Low toxicity and more biocompatible
Easy synthesis as compared to bifunctional PEGNP'c where there is requirement of vacuum environment and reaction is quite volatile requiring expertise for synthesis
Preparation is cost effective.
MUDA capped AuNC's do not require fluorescence markers and work at low pH hence can be used for bio-sensing/bio imaging and drug delivery simultaneously.
Process is environmental friendly

I claim:

1. Capped spherical nano aggregates of size 10-22 urn comprising: molecular ultra small clusters of 1-6 atoms of noble metals selected from the group consisting of Au, Ag, Pt and Pd, wherein the clusters are stabilized by a surfactant and capping groups from a reducing agent and the clusters are the nano aggregates showing UV emission at 300-335 nm, no surface plasmon resonance, and visible $2^{nd}$ harmonic emission at 590-650 nm.

2. The capped spherical nano aggregates as claimed in claim 1, wherein the reducing agent is a mild reducing agent selected from the group consisting of hydrazine hydrate or citric acid in water.

3. The capped spherical nano aggregates as claimed in claim 1, wherein the surface of the nano aggregates is stabilized and capped by a capping group from amine or dicarboxyacetone (DCA) group of a mild reducing agent and a surfactant comprising an oxyethylene group.

4. The capped spherical nano aggregates as claimed in claim 1, wherein the capping agent is mercapto undecanoic acid.

5. The capped spherical nano aggregates as claimed in claim 4, wherein mercapto undecanoic acid capped nano aggregates are stable at pH 3-4 at a temperature ranging between 25-35° C.

6. The capped spherical nano aggregates as claimed in claim 4, wherein mercapto undecanoic acid capped nano aggregates show 6 times more fluorescence intensity in comparison to amine/dicarboxyacetone capped nano aggregates.

7. The capped spherical nano aggregates as claimed in claim 1, wherein nano aggregates show green emission when a blue or a green emission filter is used.

8. A process for the preparation of spherical nano aggregates as claimed in claim 1, wherein the said process comprises the steps of:
   a) preparing a oil phase by stirring cyclohexane and non ionic surfactant Triton 100-X ($C14H22O(C2H4O)n$ (n=9-10) in ratio ranging between 52:22 wt, % to 54:24 wt % for 11-12 hrs at room temperature ranging between 25-35° C. with constant stirring and adding 7-11 wt. % n hexanol into it and stirring further for 10-12 hrs at room temperature ranging between 25-35° C.;
   b) dividing oil phase as obtained in step (a) into two equal parts;
   c) adding aqueous solution of freshly prepared 0.056 M metal salt in one part of oil phase as obtained in step (b) and stirring for 10-12 hrs;
   d) adding aqueous solution of freshly prepared 0.32 M mild reducing agent in second part of oil phase as obtained in step (b) and stirring for 10-12 hrs;
   e) combining solution as prepared in step (c) into the solution as obtained in step (d) dropwise and further stirring the solution for a period ranging between 10-20 days at, room temperature ranging between 25-35° C. to obtain solution containing nanoaggregates; and
   centrifuging solution containing nanoaggregates as obtained in step (e) at 5000-6000 rpm for 10-20 min. at room temperature ranging between 25-35° C. and washing with water and ethyl alcohol 2-3 times to obtain spherical nano aggregates.

9. The process as claimed in claim 8, wherein mild reducing agent used in step (d) is selected from the group consisting of hydrazine hydrate or citric acid in water.

10. The process as claimed in claim 8, wherein metal salt used in step (c) is auric Chloride, silver nitrate and platinum chloride.

* * * * *